US006368643B1

(12) United States Patent
Fan et al.

(10) Patent No.: US 6,368,643 B1
(45) Date of Patent: *Apr. 9, 2002

(54) ASSIMILATION OF INORGANIC SELENIUM AND ORGANIC GERMANIUM BY YEAST

(75) Inventors: David Fan, Newport Beach; Ping Yang, Fullerton; Houn Simon Hsia, Irvine, all of CA (US)

(73) Assignee: Viva America Marketing, Inc., Costa Mesa, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/298,114

(22) Filed: Apr. 23, 1999

Related U.S. Application Data

(60) Continuation-in-part of application No. 09/015,758, filed on Jan. 29, 1998, now Pat. No. 6,159,466, which is a division of application No. 08/719,572, filed on Sep. 25, 1996, now Pat. No. 6,140,107.
(60) Provisional application No. 60/082,939, filed on Apr. 24, 1998.

(51) Int. Cl.$^7$ ................................................ C12N 1/16

(52) U.S. Cl. ................ 426/62; 435/255.2; 435/255.21

(58) Field of Search ................ 424/702, 93.51; 426/62, 648, 656; 435/255.1, 255.21, 255.2

(56) References Cited

U.S. PATENT DOCUMENTS

| | | | | |
|---|---|---|---|---|
| 3,793,455 A | 2/1974 | Asai et al. | ................... | 424/287 |
| 4,530,846 A | 7/1985 | Nagodawithana et al. | .... | 426/62 |
| 5,386,046 A | 1/1995 | Arnold | ........................ | 556/89 |
| 6,140,107 A | * 11/2000 | Yang et al. | .............. | 435/255.2 |

FOREIGN PATENT DOCUMENTS

| | | | |
|---|---|---|---|
| DE | 33 45 211 A1 | | 6/1985 |
| JP | 53127882 | | 11/1978 |
| JP | 53130483 | | 11/1978 |
| JP | 54002393 | * | 1/1979 |
| WO | 97/17080 | * | 5/1997 |
| WO | 98/12925 | * | 4/1998 |

OTHER PUBLICATIONS

Schrauzer, G.N. et al. Observations on Human Selenium Supplementation. Trace Substances in Environmental Health, Jan. 13, 1979, pp. 64–67.
Schrauzer, G.N. and White, D.A., Selenium in Human Nutrition: Dietary Intakes and Effects of Supplementation; Bioinorganic Chemistry, 8, pp. 303–318 Aug. 1978.
Kumpulainen, Jorma DSc, Salmenperä, Leena MD, Siimes, Martti A. MD, Koivistoinen, Pekka DSc Perheentupa, Jaakko MD, "Selenium status of exclusively breast–fed infants as influenced by maternal organic or inorganic selenium supplementation", Amer. Jour. of Clinical Nutrition, vol. 42., No. 5, pp. 829–835, Nov. 1985.

Talaro, K. et al., "Physical and Chemical Control of Microbes" and "Environmental and Applied Microbiology" in Talaro, K. et al., Foundations in Microbiology (Wm. C. Brown Publishers,), pp. 281–282, 741–742, Jan. 1993.

Brock et al. "Enrichment Culture", In: Biology of Microorganisms. Fourth Edition, Prentice–Hall, Inc., Englewood Cliffs, NJ. pp. 617–619, Jan. 1984.

Puempel et al., "Silver tolerance and silver accumulation of microorganisms from soil material of a silver mine", Appl. Microbiol Biotechnol., 24 (3), pp. 244–247, Mar. 1984.

Barnett J.A. et al. Yeasts Characteristics abd Identification. Cambridge University Press. Second edition, pp. 595–597, Jan. 1990.

Wei X. Use of yeast for bioenrichment with germanium. Shipin Kexue (Beijing) pp. 149, 49–54, 39; Jan. 1992.

Babeva et al. Methods for Isolation and Identification of Yeasts. Publishing House "Food Industry" Moscow, pp. 9–18, Jan. 1979.

* cited by examiner

*Primary Examiner*—Keith Hendricks
(74) *Attorney, Agent, or Firm*—Lyon & Lyon LLP

(57) ABSTRACT

The yeast, Saccharomyces boulardii, has been used to invent a non-toxic selenium-germanium yeast product. Culture growth conditions can influence the biosorbent selenium and germanium uptake capacity. The invention involves assimilation of selenium and germanium by the yeast under optimal conditions of incubation time, biomass concentration, reaction pH, reaction medium, and feed rate. This yeast can assimilate higher intracellular selenium and germanium by either a one-step continuous feed-batch fermentation or a two-step continuous and semi-continuous feed-batch fermentation. The invention additionally involves the novel germanium and selenium-containing yeast.

34 Claims, No Drawings

ASSIMILATION OF INORGANIC SELENIUM AND ORGANIC GERMANIUM BY YEAST

This application is a continuation-in-part of U.S. application Ser. No. 09/015,758, filed Jan. 29, 1998, now U.S. Pat. No. 6,159,466, entitled "ORGANOMETALIC METABOLIZING YEAST," which is a divisional of U.S. application Ser. No. 08/719,572, filed Sept. 25, 1996, now U.S. Pat. No. 6,140,107, entitled "ORGANOMETALIC METABOLIZING YEAST. This application claims Provisional Application No. 60/082,939, filed on Apr. 24, 1998.

FIELD OF INVENTION

The present invention relates generally to the field of human therapeutic products, human dietary supplements, and methods for their manufacture. More specifically, the invention relates to specially formulated yeast compositions containing substantial amounts of intracellular selenium and germanium.

BACKGROUND OF THE INVENTION

Metal supplementation of the human diet is generally recognized as an important area in the field of nutritional science. Although no "RDA" minimum daily intake requirements have been officially adopted for many such compounds, research has strongly suggested that absence of some minerals, particularly metallic minerals such as selenium and germanium, can lead to improper functioning of the body's metabolic processes, and to various diseases and disorders. For example, selenium has a preventative role in the etiology of cancer and may work as a therapeutic agent against numerous tumors. [Milner and Hsu, *Inhibitory Effects of Selenium on the Growth of L1210 Leukemic Cells*, Cancer Research, May 1989, 41(5):1652–6; Goodwin et. al., *Selenium and Glutathione Peroxidase Levels in Patients with Epidermoid Carcinoma of the Oral Cavity and Oropharynx*, Cancer, Jan. 1, 1983, 51(1):110–5]. Similarly, a specific compound of germanium, carboxyethylgermanium sesquioxide, has been used as a dietary supplement for treatment of hypertension. [See, Asai, U.S. Pat. No. 3,793,455].

Nutritional supplementation of the human diet with metals, using inorganic or organometallic sources for the metals, has met with limited success. Safety and efficacy in the human metabolism of such metals has been questioned, since most inorganic forms of metals are known to have appreciable toxicity. For example, selenium is usually administered as selenium trioxide species—an agent which is extremely toxic. Similarly, inorganic germanium compounds, such as germanium dioxide and metallic germanium, are known to have inherent toxicity. In addition, inorganic forms of such metals generally have a low bioavailability, making their use in nutritional supplements questionable.

Supplementation of the human diet with metal-enriched yeast products has been sought as an improved methodology for bioavailability and law toxicity. Potential advantages of administering a metal derived from yeast as a nutritional supplement over non-yeast derived forms are that the toxicity of the metal will be lower in yeast derived organometallic compounds, and that since yeast-derived organometallic compounds are more soluble, such compounds will be better metabolized by the human body.

For example, selenium metal, usually highly toxic when administered in inorganic form such as $SeO_3Na_2$, has been shown to be more effective nutritionally when ingested as a yeast-derived substance. [See, e.g., Baerwald, *Gordian*, 94 (11):169–173 (1994)]. A method of producing selenium-enriched food yeast such as *Saccharomyces Cerevisiae* or *Candida Utilis* has been reported. When dried and fed to rats, these selenium-enriched yeast effectively prevent hepatic liver necrosis. [Reed et. al., *Yeast Tech.*, AVI Publ. Co., Conn. (1973)]. Unfortunately, this method results in the production of yeast having low selenium content as well as a relatively high extracellular concentration of inorganic selenium. U.S. Pat. No. 4,530,846 describes a method for producing a selenium-enriched yeast that yields yeast with a moderate intracellular selenium content of about 1,000 ppm. The yeast produced by this method is cultivated using a procedure that involves incremental feeding of the yeast culture. Improved methods of manufacture and special yeast stains can yield higher intracellular Selenium metal concentrations and reduced toxicity. See PCT 98/37172.

Generally, high extracellular concentrations of selenium are to be avoided, while higher intracellular concentrations are preferred because this indicates an increased relative concentration of selenium in the organic form which, as noted above, has been noted to be preferred for administrations to humans. For this reason, prior efforts at producing selenium-based yeast products have focused on the ability to provide increased intracellular concentrations of selenium. For example, U.S. Pat. No. 4,530,846 ('846) describes a method for producing a selenium-enriched yeast that yields yeast with a moderate intracellular selenium content of about 1,000 ppm. The yeast produced by this method are cultivated using a procedure that involves incremental feeding of the yeast culture. The '846 patent states: "While intracellular selenium contents of yeasts are preferably in a range of 1,000 ppm or more, preferably as high as 2,500 ppm, the process has, as its practical limitations, the capacity of the yeast to assimilate the selenium during the yeast growth cycle without adverse effects on yield due to the selenium additive to the nutrients". In addition to the recognized limitations on the ability to achieve higher concentrations of intracellular selenium, and prior art also demonstrates that yeast-derived selenium products still exhibit substantial toxicity. For example, the $LD_{50}$ the yeast product described in the '846 patent is reported to be the 7 mg per kilogram. In practice, the $LD_{50}$ rating for a product limits the amount that may be administered to a human as part of a nutritional program or as part of an overall therapy to treat a disease.

A method for preparing germanium-derived yeast has been taught by Komatsu, JP 77-46138770420. However, this method involves the preparation of germanium yeast using a highly toxic form of germanium, $GeO_2$, as the source of germanium for the feed and cultivation of the yeast. The major shortcoming of the method of Komatsu is that the yeast produced by the method has an appreciable content of highly toxic non-metabolizable germanium, and is therefore not useful as a human dietary supplement. In contrast to such inorganic forms of germanium, organic germanium compounds such as carboxyethylgermanium sesquioxide is nontoxic to the human body, having LD50 values in excess of 5 g/kg. Carboxyethylgermanium sesquioxide has been used to prepare a germanium-derived yeast. [See U.S. application Ser. No. 08/661,089, now U.S. Pat. No. 6.017,526].

Although yeast has been used to assimilate metals, beneficial combinations of metals derived from yeast are needed as are methods to produce such compositions, specifically selenium-germanium enriched yeast where: (1) the yeast product contains high intracellular selenium and germanium content; (2) the yeast product is substantially non-toxic to the human body at concentrations suitable for dietary supplementation or therapy; and (3) the chemical form of selenium and germanium produced by the selenium-germanium enriched yeast is highly metabolizable by the human body, and thus a useful and significantly improved agent for the nutritional supplementation of the human diet or for administration as a therapeutic agent, alone or in combination with other agents, in the treatment of disease.

SUMMARY OF THE INVENTION

The present invention overcomes the shortcomings of the prior art by providing a method for producing a selenium-germanium enriched yeast product that has a high intracellular content of organically bound trivalent selenium and germanium in high biological activity in a non-toxic form, providing a nutritional supplement which incorporates the selenium-germanium enriched yeast to promote good nutrition, and providing a therapeutic agent that can be administered for the treatment of disease. The present invention also includes the novel germanium and selenium-containing yeast, and the selenium-germanium yeast product in a form suitable for administration.

DETAILED DESCRIPTION OF THE PREFERRED EMBODIMENTS

The present invention relates to methods of cultivating yeast using selenium and germanium compounds resulting in a dried selenium-germanium enriched yeast product with high biological activity, nutritional supplements comprising this dried yeast product, as well as uses of such dried yeast product to supplement the human diet.

In a preferred embodiment of the present invention, the process for preparing the selenium-germanium enriched yeast product that has a high intracellular content of organically bound trivalent selenium and germanium in a highly biologically active and non-toxic form is accomplished by using a one-step continuous feed-batch fermentation method, which comprises a process wherein the steps are selected from the following:

(1) preparing a yeast growth medium;

(2) preparing an aqueous stock solution of selenium salt;

(3) preparing an aqueous stock solution of germanium salt;

(4) mixing the selenium and germanium stock solutions with the yeast growth medium to form a selenium-germanium growth mixture;

(5) adding the selenium-germanium growth mixture, preferably by incremental addition, to a live yeast culture to form a selenium-germanium yeast growth solution;

(6) incubating the selenium-germanium yeast growth solution to induce yeast cell growth;

(7) isolating and concentrating the yeast cells from the selenium-germanium yeast growth solution;

(8) washing the recovered yeast cells to remove extracellular selenium and germanium; and (9) processing, i.e., pasteurizing and/or drying the washed yeast cells.

The growth medium used in the first preparing step of the one-step continuous feed-batch fermentation method of the present invention may include a source of carbohydrate such as molasses or glucose and nutrient salts such as potassium chloride, magnesium sulfate, and nitrogen, as well as phosphorous sources such as ammonium dihydrogen phosphate, ammonia, and phosphoric acid. Numerous other growth media that are known to support the growth of yeast from the Saccharomyces family may be used and could be readily selected by one of skill in the art. In a preferred form, a mixture of different growth media may be used.

In addition, numerous vitamins and minerals may optionally be added to the yeast growth media. Such vitamins and minerals are selected from those known in the art to help sustain proper yeast growth, including but not limited to biotin, vitamin $B_1$, vitamin $B_6$, calcium pantothenoate, inositol, copper, copper sulfate, zinc, zinc sulfate, iron, and iron sulfate.

The second preparing step involves preparing a selenium stock solution by dissolving a selenium salt in distilled water and filtering the resulting selenium solution. The selenium may be in the form of an amorphous solid or an organoselenium compound. In a preferred form, sodium selenate may be used. In another preferred form, sodium selenite may be used. Preferably, a cellulose acetate filter membrane [Corning Scientific Co.] is used to filter the aqueous selenium solution. The resultant filtered selenium stock solution has a selenium concentration of about 100 ppm to about 80,000 ppm, most preferably from about 2,000 ppm to 60,000 ppm.

The third preparing step involves the preparation of a germanium stock solution. The germanium solution is prepared by first dissolving an organic germanium compound, preferably dicarboxyethylgermanium sesquioxide or carboxyethylgermanium sesquioxide, in distilled water. This solution is then heated to about 30 to 70 degrees Celsius, most preferably between about 40 to 60 degrees Celsius, and incubated for about 5 minutes to about 120 minutes, most preferably between about 30 minutes to about 60 minutes. The resulting homogeneous solution is then allowed to cool down, and its pH is adjusted to a value between about 4 to about 7, or more preferably about 4.5 to about 6, and most preferably to about 5. The pH adjusted homogeneous solution is then filtered, preferably using a cellulose acetate filter membrane [Corning Scientific Co.]. The resultant filtered germanium stock solution has a germanium concentration of about 100 ppm to about 30,000 ppm, more preferably from about 500 ppm to about 25,000 ppm, and most preferably from about 1,000 ppm to about 20,000 ppm.

In the mixing step of the one-step continuous feed-batch fermentation method of the present invention, the selenium and germanium stock solutions are first added to the yeast growth medium. The combination of the solutions and the growth medium is then well mixed by gentle shaking action or stirring for between about 1 and about 30 minutes to form a selenium-germanium growth mixture.

In the adding step, the selenium-germanium growth mixture is added to live yeast cells to make a selenium-germanium yeast growth solution having a selenium concentration of about 100 ppm to about 20,000 ppm selenium, more preferably between about 200 ppm to about 5,000 ppm, and most preferably between about 250 ppm to about 300 ppm. The selenium-germanium yeast growth solution also contains a germanium concentration of about 100 ppm to about 30,000 ppm, more preferably between about 500 ppm to about 20,000 ppm, and most preferably between about 2,000 ppm to about 2,300 ppm.

The adding step preferably involves adding the selenium-germanium growth mixture to the live yeast culture incrementally. The adding step preferably takes place under a controlled pH of from about 4.2 to about 6.0, and preferably from about 4.5 to 5.3. This adding step also preferably takes place at a temperature from about 20° C. to about 35° C., and preferably from about 28° C. to about 32° C.

The yeast employed in the adding step is preferably a food grade or edible yeast, and most preferably *Saccharomyces boulardii* sequela PY31. The novel strain of yeast, Saccharomyces boulardii sequela PY31, is described in a pending application U.S. Ser. No. 08/719,572, now U.S. Pat. No. 6,140,107, see PCT 98/37172 which is herein fully incorporated by reference.

In the incubating step, the incubation may occur at an agitation of about 500 rpm to about 1000 rpm for a period of about 5 hours to about 75 hours, more preferably at an agitation of about 600 rpm to about 900 rpm for a period of about 10 hours to about 60 hours, and most preferably at an agitation of about 800 rpm for a period of about 16 hours to about 22 hours. This incubation occurs at a temperature of about 25° C. to about 30° C., and preferably about 30° C. In addition, this incubation takes place under a controlled pH of from about 4.2 to about 6.0, preferably from about 4.5 to 5.3, and most preferably at about 4.5.

The yeast cells are then recovered, isolated, concentrated by centrifugation or other equivalent means, and washed successively with water to remove extracellular selenium and germanium, as well as other solubles. The centrifuged yeast cells may also be washed with aqueous solvent, such as a buffered aqueous solution that optionally contains chelating agents such as EDTA. The resulting yeast cream of the washed yeast cells has a significant amount of intracellular selenium and germanium content and is then pasteurized and dried to kill the yeast. Processes for drying the yeast include drum drying and other techniques known in the art. The preferred concentration of intracellular selenium in the dried yeast is from about 600 $\mu$g to about 2,000 $\mu$g selenium per gram of dried yeast solids. The preferred concentration of intracellular germanium in the dried yeast produced using the one-step continuous feed-batch fermentation method is from about 600 $\mu$g to about 1,500 $\mu$g germanium per gram of dried yeast solids. The resulting yeast powder is then ready for use as a dietary supplement of organically bound, assimilable selenium and germanium.

In another preferred embodiment of the present invention, the process for preparing the selenium-germanium enriched yeast product that has a high intracellular content of organically bound trivalent selenium and germanium in a highly biologically active and non-toxic form is accomplished by using a two-step continuous and semi-continuous feed-batch fermentation method, which comprises the steps of:

(1) preparing a yeast growth medium;

(2) preparing an aqueous stock solution of selenium salt;

(3) preparing an aqueous stock solution of germanium salt;

(4) mixing the selenium and germanium stock solutions separately with the yeast growth medium to form a selenium growth mixture and a germanium growth mixture;

(5) adding the selenium growth mixture, preferably by incremental addition, to a live yeast culture to form a selenium yeast growth solution;

(6) incubating the selenium yeast growth solution to induce yeast cell growth;

(7) isolating and concentrating the yeast cells from the selenium yeast growth solution to form a selenium yeast cream;

(8) adding the germanium growth mixture, preferably by incremental addition, to the selenium yeast cream to form a selenium-germanium yeast growth solution;

(9) incubating the selenium-germanium yeast growth solution to induce yeast cell growth;

(10) isolating and concentrating the yeast cells from the selenium-germanium yeast growth solution;

(11) washing the recovered yeast cells to remove extracellular selenium and germanium; and

(12) pasteurizing and/or drying the washed yeast cells.

The first three preparing steps of the two-step continuous and semi-continuous feed-batch fermentation method are essentially the same as those of the one-step continuous feed-batch fermentation method described above.

Unlike the one-step method, however, the two-step method allows the yeast to absorb and assimilate selenium first. The resulting selenium yeast is then allowed to absorb and assimilate germanium.

Therefore, with the exclusion of the germanium stock solution in the growth mixture, steps (4) through (7) of the two-step method are accomplished in the same manner as those of the one-step method described above, and with the same process conditions as those used for the one-step method. Such conditions include feed rate of the growth mixture, reaction pH, incubation time, and temperature.

The germanium growth mixture is then added to the isolated and concentrated selenium yeast cream, preferably by incremental addition, to make a selenium-germanium yeast growth solution having a germanium concentration of about 100 ppm to about 30,000 ppm, more preferably between about 500 ppm to about 20,000 ppm, and most preferably between about 3,500 to about 5,000 ppm. The reaction conditions remain the same as those used to assimilate selenium.

The selenium-germanium yeast growth solution is then incubated at an agitation of about 150 rpm to 300 rpm and at a temperature between about 25° C. to 30° C., most preferably at an agitation of about 200 rpm and a temperature of about 30° C. The incubation time is between about 5 hours and about 120 hours, more preferably from about 20 hours to about 90 hours, and most preferably from about 48 hours to about 72 hours.

The yeast cells are then isolated, concentrated, washed and dried as described in the one-step continuous feed-batch fermentation method. The preferred concentration of intracellular selenium in the dried yeast is from about 600 $\mu$g to about 2,000 $\mu$g selenium per gram of dried yeast solids. The preferred concentration of intracellular germanium in the dried yeast produced using the one-step continuous feed-batch fermentation method is from about 1,000 $\mu$g to about 3,000 $\mu$g germanium per gram of dried yeast solids. The resulting yeast powder is then ready for use as a dietary supplement of organically bound, assimilable selenium and germanium.

In still another preferred embodiment of the present invention, the two-step continuous and semi-continuous feed-batch fermentation method is modified such that the yeast is allowed to react with germanium before it reacts with selenium.

The present invention also relates to the use of the dried selenium-germanium enriched yeast products as dietary supplements. To prepare the yeast compositions of the invention for use as a dietary supplement, the dried yeast product is combined as the active ingredient in intimate admixture with a suitable carrier according to conventional compounding techniques. This carrier may take a wide variety of forms depending upon the form of preparation desired for administration, e.g., oral, sublingual, nasal, or parenteral.

In preparing the compositions in oral dosage form, any of the usual pharmaceutical media may be employed. For oral liquid preparations (e.g., suspensions, elixirs, and solutions), media containing for example, water, oils, alcohols, flavoring agents, preservatives, coloring agents and the like may be used. Carriers such as starches, sugars, diluents, granulating agents, lubricants, binders, disintegrating agents, and the like may be used to prepare oral solids (e.g., powders, capsules, pills, and tablets). Controlled release forms may also be used. Because of their ease in administration, tablets, pills, and capsules represent advantageous oral dosage unit forms, in which cases solid pharmaceutical carriers are obviously employed. If desired, tablets may be sugar coated or enteric coated by standard techniques.

For parenteral products the carrier will usually comprise sterile water, although other ingredients may be included, e.g., to aid solubility or for preserved purposes. Injectable suspensions may also be prepared, in which case appropriate liquid carriers, suspending agents, adjuvants, and the like may be employed.

The following examples are illustrative only and do not limit the invention in any fashion.

EXAMPLE 1

Yeast growth medium and stock solutions are prepared for both the one-step continuous feed-batch fermentation method and the two-step continuous and semi-continuous feed-batch fermentation method as follows:

Medium and Cultural Conditions

Yeast stocks were maintained at 30° C. on malt agar (DIFCO) or sabouraud dextrose agar (DIFCO). For most processes, yeast cultures were grown in a molasses medium with a pH of 5.0 having the following composition (g $L^{-1}$): 79 °Brix TCT molasses (LSI, Emeryville, Calif.), 80.8; KCl, 0.33; $MgSO_4$, 0.33; $NH_4H_2PO_4$, 3.6. Some cultures were grown in a liquid basal medium which had the following composition (g $L^{-1}$): D-glucose, 30.0; urea, 3.23; $MgSO_4$, 0.57; KCl, 0.33; $NaH_2PO_4$, 1.5; sodium citrate, 3.75; yeast extract, 0.75. The pH was adjusted to 5.0 using HCl. The cultures were allowed to grow prior to use. Cell numbers and percentage of budding cells and dead cells were determined using a haemocytometer after appropriate dilution with distilled water and staining with 0.4% trypan blue solution (Sigma, St. Louis, Mo.). The size of yeast populations in aqueous suspensions were determined using optical density (OD590) measurements.

Preparation of Germanium Stock Solution for Yeast Cell Assimilation

A stock solution (10,000 ppm) of dicarboxyethylgermaniumsesquioxide was prepared by adding 10.0 g of dicarboxyethylgermaniumsesquioxide (Westar Nutrition Corp., Costa Mesa, Calif.) to 900 ml of distilled water at room temperature. The resulting mixture was warmed to 60° C. for 1 hour. The homogeneous solution was cooled and its pH adjusted to 5.0 with 50% NaOH and filled to 1 liter, which was then filtered through a 0.45-µm-pore-size cellulose acetate filter membrane (Corning).

Preparation of Selenium Stock Solution for Yeast Cell Assimilation

A stock solution (60,000 ppm) of sodium selenate was prepared by adding 60.0 g sodium selenate (Alfa AESAR) to 900 ml of distilled water at room temperature. The resulting mixture was well-mixed, filled to 1 liter, and then filtered through a 0.45 µm-pour-size cellulose acetate filter membrane (Corning).

EXAMPLE 2

Three experiments (Experiments 1–3, Table 1) were conducted to produce a dried yeast product having intracellular content of selenium and germanium, using the one-step continuous feed-batch fermentation method.

The yeast strain (YP3-1), *Saccharomyces boulardii* Sequela, was allowed to grown to $1-2\times10^6$ cell/ml in the sabouraud broth medium. The yeast cells were then transferred to a fermentor (BIOFLO 3000 FERMENTOR, New Brunswick Scientific, Edison, N.J.), followed by incremental feeding of a TCT molasses (LSI, Emeryville, Calif.) mixture, vitamin mixture, sodium selenate (Alfa AESAR) and dicarboxyethylgermanium sesquioxide (Westar Nutrition Corp., Costa Mesa, Calif.). Table 1 shows the amount of sodium selenate, dicarboxyethylgermanium sesquioxide and each of the yeast growth nutrients used. The resulting mixture contained 251 ppm of selenium and 2150 ppm of germanium. The mixture also contained 6.9–7.9°Brix of TCT molasses (e.g., 7.9 °Brix for Experiment 1, and 6.9 °Brix for Experiments 2 and 3). This mixture was then incubated at the fermentor at an agitation of 800 rpm, pH 4.5, DO>30, air and $O_2$ 8 L/min, at 30° C. After certain effective incubation time (See Table 1), the mixture was centrifuged, the supernatant removed, and the yeast cells washed once with 0.025 M EDTA (pH=6) solution, and five times with distilled water. The resulting yeast cream was dried in a 90° C. oven for 2 days.

The resulting dried yeast product contained significant amount of intracellular content of selenium and germanium, as shown in Table 1.

TABLE 1

One-step continuous feed-batch fermentation.

| Experiment | 1 | 2 | 3 | Average |
|---|---|---|---|---|
| TCT molasses mix | 2.5 L of 31.7 Brix | 2.3 L of 30 Brix | 2.3 L of 30 Brix | |
| Vitamin mix (ml) | 6 | 6 | 6 | |
| dicarboxyethyl-germanium sesquioxide (g) | 50 | 50 | 50 | |
| Sodium selenate (g) | 6 | 6 | 6 | |
| Total work volume (L) | 10 | 10 | 10 | |
| Effective Fermentation Time (hr) | 24 | 24 | 21 | 23 |
| Total yeast cell × $10^7$/ml | 21 | 18 | 23.3 | 20.8 |
| Dead cell % | 0.28 | 0.14 | 0 | 0.14 |
| Wet cell (g) | 714 | 808 | 772 | 764.7 |
| Dry cell (g) | 198 | 208 | 187 | 197.7 |
| [Se] ppm in dried yeast | 989 | 802 | 622 | 804.3 |
| [Ge] ppm in dried yeast | 623 | 720 | 680 | 674.3 |

EXAMPLE 3

Three experiments (Experiments 4–6, Table 2) were conducted to produce a dried yeast product having intracellular content of selenium and germanium, using the two-step continuous and semi-continuous feed-batch fermentation method.

The yeast strain (YP3-1), *Saccharomyces boulardii* Sequela, was allowed to grown to $1-2\times10^6$ cell/ml in the sabouraud broth medium. The yeast cells were then transferred to a fermentor (BIOFLO 3000 FERMENTOR, New Brunswick Scientific, Edison, N.J.), followed by incrementally feeding with a molasses (LSI, Emeryville, Calif.) mixture, vitamin mixture, sodium selenate (Alfa AESAR).

Table 2 shows the amount of sodium selenate and each of the yeast growth nutrients used. The resulting mixture, containing 251 ppm of selenium and 6.9–7.9°Brix of TCT molasses (e.g., 7.9°Brix for Experiment 1, and 6.9°Brix for Experiments 2 and 3), was incubated at the fermentor at an agitation of 800 rpm, pH 4.5, DO>30, air and O2 8 L/min and temperature 30° C. After certain effective incubation time (See Table 2), this mixture was centrifuged, the supernatant removed, then the yeast cream containing selenium was washed once with sterile water.

The Ge uptake was prepared as follows. The feeding solution containing a 32° Brix molasses (LSI, Emeryville, Calif.) mixture, vitamin mixture, dicarboeyethylgermanium-sesquiocide (Westar Nutrition Corp., Costa Mesa, Calif.) solution, and sterile water (shown in Table 2) were fed to the yeast cream at every four hours of fermentation. The resulting mixture containing 4300 ppm of germanium, and 6.2° Brix of TCT molasses was incubated at a shaker (New Brunswick Scientific, Edison, N.J.) at 200 rpm, and 30° C. After 2 days of incubation, this mixture was centrifuged, the supernatant removed, then the yeast cells were washed once with 0.025 M EDTA (pH=6) solution, and then five times with distilled water. The resulting yeast cream was dried in a 90° C. oven for 2 days.

The resulting dried yeast product contained significant amount of intracellular content of selenium and germanium, as shown in Table 2.

TABLE 2

Two-step continuous and semi-continuous feed-batch fermentation

| Experiment | 4 | 5 | 6 | Average |
|---|---|---|---|---|
| TCT molasses mix | 2.5 L of 31.7 Brix | 2.5 L of 32 Brix | 2.5 L of 32 Brix | |
| Vitamin mix (ml) | 6 ml | 6 ml | 6 ml | |
| Sodium selenate (g) | 6 | 6 | 6 | |
| Total work volume (L) | 10 | 10 | 10 | |
| Effective Fermentation Time (hr) | 23 | 22 | 22 | 22.3 |
| Total yeast cell × 10$^7$/ml | 12.3 | 20 | 20.3 | 17.5 |
| Dead cell % | 0.2 | 0 | 0.29 | 0.16 |
| Wet cell (g) | 745.5 | 763 | 695 | 734.5 |
| Dry cell (g) | 187.9 | 150 | 159.7 | 165.9 |
| [Se] ppm in yeast | 720 | 802 | 715 | 745.7 |
| Dicarboxyethyl-germanium sesquioxide (g) | 14.88 | 12.2 | 11 | |
| TCT Molasses (32 Brix) | 268 ml | 275 ml | 260 | |
| [Ge] ppm in yeast | 1415.9 | 1376.9 | 1300 | 1364.3 |

EXAMPLE 4

The selenium and germanium concentration in the final dried yeast product for both the one-step continuous feed-batch fermentation method and the two-step continuous and semi-continuous feed-batch fermentation method is calculated according to the following.

Prior to analysis, 1.0 g of the dried yeast product was added to 5 ml concentrated HNO$_3$ and was left to stand overnight. The mixture was the placed in a boiling water bath for four hours. After removal and subsequent cooling, distilled water was added in sufficient amount to fill to 50 ml. The resultant solution was then filtered through a #2 Whitman filter paper. Its selenium content was measured using an atomic absorption spectrometer (Perkin Elmer, Model 3100, Norwalk, Conn.) set at a wavelength of 196.0 nm and a selenium lamp current at 16 mA. The sample was measured for its germanium content at a wavelength of 265.7 nm, a slit width of 0.2 nm, and a germanium lamp current at 35 mA. Tables 1 and 2 above show the Ge and Se content of the yeast in parts per million (ppm).

There will be various modifications, improvements, and applications of the disclosed invention that will be apparent to those of skill in the art, and the present application encompasses such embodiments to the extent allowed by law. Although the present invention has been described in the context of certain preferred embodiments, the full scope of the invention is not so limited, but is in accord with the scope of the following claims.

What is claimed is:

1. A method for producing a dried yeast product enriched with intracellular content of selenium and germanium comprising the steps of:
    preparing a yeast growth medium;
    preparing an aqueous selenium stock solution;
    preparing an aqueous germanium stock solution;
    mixing the selenium and germanium stock solutions with the yeast growth media to form a selenium-germanium growth mixture;
    adding the selenium-germanium growth mixture to a live *Saccharomyces boulardii sequela* PY31 (ATCC No. 74,366) culture to form a selenium-germanium yeast growth solution;
    incubating the selenium-germanium yeast growth solution;
    isolating and concentrating the yeast cells from the selenium-germanium yeast growth solution;
    washing the recovered yeast cells; and
    drying the washed yeast cells.

2. The method of claim 1 wherein said yeast growth medium is selected from the group consisting of Brix molasses, sabouraud broth, glucose media, and potato dextrose broth.

3. The method of claim 1 wherein said yeast growth medium comprises a mixture of different yeast growing nutrients.

4. The method of claim 1 wherein said aqueous selenium stock solution comprises a selenium compound diluted in distilled water selected from the group consisting of a selenium salt and an organoselenium species.

5. The method of claim 1 wherein the second preparing step comprises adding between about 100 ppm to about 80,000 ppm selenium to distilled water and filtering through a cellulose acetate filter.

6. The method of claim 1 wherein the step of preparing said aqueous germanium stock solution comprises:
    diluting germanium sesquioxide in distilled water;
    heating the solution to between about 35° C. to about 100° C.;
    incubating the diluted germanium sesquioxide to form a homogeneous solution;
    cooling the homogeneous solution and adjusting the pH to between about 4.0 to about 6.0
    filtering the homogeneous solution.

7. The method of claim 1 wherein the step of preparing an aqueous germanium stock solution is comprised of adding between about 100 ppm to about 40,000 ppm germanium to distilled water.

8. The method of claim 1 wherein the step of adding the selenium-germanium growth mixture to the live yeast culture is performed incrementally.

9. The method of claim 1 wherein the incubating step comprises incubation for about 5 hours to about 75 hours.

10. The method of claim 1 wherein the incubating step comprises incubation at about 25° C. to about 30° C.

11. The method of claim 1 wherein the incubating step comprises incubation at an agitation of about 500 rpm to about 1000 rpm.

12. The method of claim 1 wherein the incubating step comprises incubation at a pH of between about 4.0 to 6.0.

13. The method of claim 1 wherein the isolating and concentrating step comprises centrifugation.

14. The method of claim 1 wherein the washing step comprises washing the isolated yeast cells at least once with a buffered aqueous solvent.

15. A method for producing a dried yeast product enriched with intracellular content of selenium and germanium comprising the steps of:

preparing a yeast growth medium;

preparing an aqueous selenium stock solution;

preparing an aqueous germanium stock solution;

mixing the selenium and germanium stock solutions separately with the yeast growth media to form a selenium growth mixture and a germanium growth mixture;

adding the selenium growth mixture to a live *Saccharomyces boulardii sequela* PY31 (ATCC No. 74,366) culture to form a selenium yeast growth solution;

incubating the selenium yeast growth solution with agitation;

isolating and concentrating the yeast cells from the selenium yeast growth solution to form a selenium yeast cream;

adding the germanium growth mixture to the selenium yeast cream to form a selenium-germanium yeast growth solution;

incubating the selenium-germanium yeast growth solution;

isolating and concentrating the yeast cells from the selenium-germanium yeast growth solution;

washing the recovered yeast cells; and drying the washed yeast cells.

16. The method of claim 15 wherein said yeast growth medium is selected from the group consisting of Brix molasses, sabouraud broth, glucose media, and potato dextrose broth.

17. The method of claim 15 wherein said yeast growth medium comprises a mixture of different yeast growing nutrients.

18. The method of claim 1 wherein said aqueous selenium stock solution comprises a selenium compound diluted in distilled water selected from the group consisting of a selenium salt and an organoselenium species.

19. The method of claim 1 wherein the step of preparing aqueous selenium stock solution comprises adding between about 100 ppm to about 80,000 ppm selenium to distilled water and filtering.

20. The method of claim 1 wherein said aqueous germanium stock solution comprises further steps of:

diluting germanium sesquioxide in distilled water;

heating the solution to between about 35° C. to about 70° C.;

incubating the diluted germanium sesquioxide to form a homogeneous solution;

cooling the homogeneous solution and adjusting the pH to between about 4.0 to about 6.0;

filtering the homogeneous solution.

21. The method of claim 1 wherein the third preparing step comprises adding between about 100 ppm to about 40,000 ppm germanium to distilled water.

22. The method of claim 16 wherein the step of adding the selenium growth mixture to said live yeast culture is incremental.

23. The method of claim 15 wherein the first incubating step comprises incubation for about 5 hours to about 75 hours.

24. The method of claim 15 wherein the first incubating step comprises incubation at about 25° C. to about 30° C.

25. The method of claim 15 wherein the first incubating step comprises agitation of about 500 rpm to about 1000 rpm.

26. The method of claim 15 wherein the first incubating step comprises incubation at a pH of between about 4.0 to about 6.0.

27. The method of claim 15 wherein the first isolating and concentrating step comprises centrifugation.

28. The method of claim 15 wherein the second incubating step comprises incubation for about 5 hours to about 120 hours.

29. The method of claim 15 wherein the first incubating step comprises incubation at about 25° C. to about 30° C.

30. The method of claim 15 wherein the first incubating step comprises incubation at an agitation of about 150 rpm to about 300 rpm.

31. The method of claim 15 wherein the second isolating and concentrating step comprises centrifugation.

32. The method of claim 15 wherein the washing step comprises washing the isolated yeast cells at least once with a buffered aqueous solvent.

33. The method of claim 10 wherein said intracellular selenium content is in the range of 50 ppm to 2,000 ppm by weight.

34. The method of claim 10 wherein the intracellular germanium content is in the range of 50 ppm to 2,000 ppm by weight.

* * * * *